(12) United States Patent
Krämer

US007683040B2

(10) Patent No.: US 7,683,040 B2
(45) Date of Patent: Mar. 23, 2010

(54) INTRANASAL FORMULATION OF ROTIGOTINE

(75) Inventor: Robert Krämer, Köln (DE)

(73) Assignee: SRZ Properties, Inc., Wilmington, DE (US)

( * ) Notice: Subject to any disclaimer, the term of this patent is extended or adjusted under 35 U.S.C. 154(b) by 457 days.

(21) Appl. No.: 10/545,530

(22) PCT Filed: Dec. 22, 2004

(86) PCT No.: PCT/EP2004/014626

§ 371 (c)(1), (2), (4) Date: Jul. 17, 2006

(87) PCT Pub. No.: WO2005/063236

PCT Pub. Date: Jul. 14, 2005

(65) Prior Publication Data

US 2007/0191308 A1 Aug. 16, 2007

(30) Foreign Application Priority Data

Dec. 23, 2003 (EP) .................................. 03029680

(51) Int. Cl.
*A61K 31/724* (2006.01)
*A61K 31/381* (2006.01)

(52) U.S. Cl. ........................................ 514/58; 514/438

(58) Field of Classification Search .................. None
See application file for complete search history.

(56) References Cited

U.S. PATENT DOCUMENTS

| | | | |
|---|---|---|---|
| 4,755,535 A | 7/1988 | Minaskanian et al. | 514/947 |
| 4,847,253 A | 7/1989 | Buonamici et al. | 514/253 |
| 4,902,676 A | 2/1990 | Peck et al. | 514/29 |
| 4,992,422 A | 2/1991 | Minaskanian et al. | 514/24 |
| 5,034,386 A | 7/1991 | Peck et al. | 514/212 |
| 5,043,441 A | 8/1991 | Peck et al. | 540/526 |
| 5,073,544 A | 12/1991 | Peck et al. | 514/24 |
| 5,108,991 A | 4/1992 | Rajadhyaksha | 514/29 |
| 5,218,113 A | 6/1993 | Minaskanian et al. | 540/485 |
| 5,308,625 A | 5/1994 | Wong et al. | 424/447 |
| 5,472,946 A | 12/1995 | Peck et al. | 514/29 |
| 5,614,518 A | 3/1997 | Leeson et al. | 514/234.5 |
| 5,756,483 A | 5/1998 | Merkus | 514/58 |
| 5,771,890 A | 6/1998 | Tamada | 128/635 |
| 6,086,905 A | 7/2000 | Peck et al. | 424/406 |
| 6,687,522 B2 | 2/2004 | Tamada | 600/347 |
| 7,038,085 B2 | 5/2006 | Rariy et al. | 564/165 |
| 2003/0124191 A1 | 7/2003 | Besse et al. | 424/489 |
| 2003/0166709 A1 | 9/2003 | Rimpler et al. | 514/447 |
| 2004/0034083 A1 | 2/2004 | Stephenson et al. | 514/406 |
| 2004/0110673 A1 | 6/2004 | Steinkasserer et al. | 514/12 |
| 2004/0110763 A1 | 6/2004 | Akahane et al. | 514/252.04 |
| 2004/0142904 A1 | 7/2004 | Rariy et al. | 514/63 |
| 2004/0209861 A1 | 10/2004 | Benavides et al. | 514/210.01 |
| 2005/0032873 A1 | 2/2005 | Hatzenbuhler et al. | 514/414 |
| 2005/0107397 A1 | 5/2005 | Galambos et al. | 514/255.03 |
| 2005/0182090 A1 | 8/2005 | Mierau et al. | 514/304 |

FOREIGN PATENT DOCUMENTS

| | | |
|---|---|---|
| CA | 2532859 | 2/2005 |
| CA | 2547820 | 6/2005 |
| CA | 2568850 | 2/2006 |
| EP | 1 256 339 | 11/2002 |
| WO | WO 94/07468 | 4/1994 |
| WO | WO 94/22445 | 10/1994 |
| WO | WO 96/00110 | 1/1996 |
| WO | WO 97/29735 | 8/1997 |
| WO | WO 99/49852 | 10/1999 |
| WO | WO 2005/063236 | 7/2005 |
| WO | WO 2006/050976 | 3/2006 |

OTHER PUBLICATIONS

Merkus, P. et al "Classification of cilio-inhibiting effects of nasal drugs" The Laryngoscope (2001) vol. 111, pp. 595-602.*
Arora, P. et al "Permeability issues in nasal drug delivery" Drug Delivery Today (2002) vol. 7, No. 18, pp. 967-975.*
Challa, R. et al "Cyclodextrins in drug delivery . . . " AAPS PharmSciTech (2005) vol. 6, No. 2, pp. E329-E357.*
AADAC Alberta Alcohol and Drug Abuse Commission (2004) Beyond the ABCS—Amphetamines: www.aadac/.com.
Burn (2000) *The Pharmaceutical Journal* 264: 476-479.
Collado-Seidel et al. (1999) *CNS Drugs* Jul; 12(1):9-20.
Duarte J et al. (1995) *Journal of Pharmacy Technology*, 11, 226-228.
Hauser et al. (2004) *Neurol. Clin.* 22: S149-S166.
Kelly (1997) *Pharmacology Therapeutics* 74(3): 299-316.
Korczyn et al. (2002) *Drugs* 62(5): 775-786.
Levien (2005) *Advances in Pharmacy* 3(1): 62-92.
Li et al. (2001) Pharm. Research 18(11): 1509-1513.
Menon et al. (1972) *Eur. J. Pharmacol.* 19:43-51.
Merkus et al. (1999) *Advanced Drug Delivery Reviews*, 36, 41-57.
Mucke HAM (2003) *IDrugs*, 6(9), 894-899.
Park (2002) Drug Delivery Technology 2(5), Jul./Aug., http://www.drugdeliverytech.com/cgi-bin/issues.cgi?idIssue=6 and http://www.drugdeliverytech.com/cgi-bin/articles.cgi?idArticle=60.
Silber et al. (2001) *Sleep* 24 (Abstract Suppl) A18.
Swart (1992) *Internaional J. Pharmaceutics* 88: 165-170.
Swart et al. (1993) *Toxicology Methods* 3(4): 279-290.
Swart et al. (1995) *Pharmaceutical Sciences*, 1, 437-440.
Tuite (2003) *Expert Opin. Investig. Drugs* 12(8): 1335-1352.
Van de Donk et al. (1980) *Rhinology*, 8, 93-104.
Van Laar et al. (1992) *Ned Tijdschr Geneeskd*, 136, nr. 14, 702-704, In Dutch abstract only.
van Riezen (1977) *British J. Pharmacology* 60:521-528 PMID 907867.
Abe, et al. (1995) Chem. Pharm. Bull. 43(12):2232-2237.
Van der Weide, et al. (1988) "The enantiomers of the D-2 dopamine receptor agonist N-0437 discriminate between pre- and postsynaptic dopamine receptors." Eur J Pharmacol 146:319-326.

* cited by examiner

*Primary Examiner*—Leigh C Maier
(74) *Attorney, Agent, or Firm*—Harness, Dickey & Pierce, P.L.C.

(57) ABSTRACT

This invention pertains to a liquid intranasal pharmaceutical formulation comprising a pharmaceutically acceptable acid addition salt of rotigotine and α-cyclodextrin, preferably in the form of a buffered aqueous solution having a viscosity of 0.5-1.5 mm²/s.

17 Claims, No Drawings

INTRANASAL FORMULATION OF ROTIGOTINE

This application is a U.S. national stage filing under 35 U.S.C. §371 of International Application No. PCT/EP2004/014626 filed on 22 Dec. 2004, which claims priority to European Application No. 03029680.0 filed on 23 Dec. 2003.

FIELD OF THE INVENTION

The present invention relates to an intranasal pharmaceutical formulation containing a pharmaceutically acceptable salt of rotigotine. Such intranasal formulations are useful in the treatment of diseases where the administration of rotigotine is beneficial, in particular in the treatment of morbus Parkinson and other dopamine-related disorders.

BACKGROUND OF THE INVENTION

It is known that dopamine D2 agonists such as apomorphine or rotigotine may in principle be used to treat morbus Parkinson and other diseases for which an increase of the dopamine level is beneficial such as the restless leg syndrome (RLS). However, due to the very high first-pass effect of most of these dopamine agonists and the problem that many Parkinson patients develop some kind of drug tolerance against these drugs, the development of a safe and effective pharmaceutical formulation by which controlled amounts of drug can be administered is far from trivial.

Rotigotine (5,6,7,8-tetrahydro-6-[propyl-[2-(2-thienyl) ethyl]amino]-1-naphthalenol, sometimes also designated as N-0923) and its pharmaceutically acceptable salts have been previously administered to patients mainly in the form of transdermal delivery systems (see e.g. WO 94/07468, WO 99/49852, EP-A-1 256 339). However, there was also at least one attempt of an intranasal administration of this drug (Swart et al., Pharmaceutical Sciences 1995, 1: 437-440). Swart et al. administered a solution of rotigotine hydrochloride in a 1:1 mixture of polyethylenglycol (PEG) 400 and water to male Albino Wistar rats. While they observed an improved bioavailability of rotigotine after buccal, nasal or rectal administration compared with oral dosing in the rat, they also observed that the bioavailability for the nasal dosing was "somewhat disappointing" when compared with the results described for other lipophilic drugs. Swart et al. suggested that the relatively low bioavailability they observed may be explained by a low absorption or rapid metabolic conversion of the drug in the nasal mucosa. These authors further stated that as of 1995 no information was available about the influence of rotigotine on the ciliary function of the nasal mucosa. In their view, nasal medication may change or even destroy the epithelial cells, with the recovery taking a few hours to a few months depending on the agent (Van Donk et al., Rhinology 18: 93-104).

In view of this rather discouraging report, it is perhaps not very surprising that the nasal administration of rotigotine does not seem to have been further attempted in the years after 1995 until the present invention was made. The state of information on the influence of rotigotine on the ciliary function of the nasal mucosa remained basically unchanged since these days.

US-A-2003-0,124,191 discloses a pharmaceutical composition in powder form that is intended for administration through the mucosa. A large variety of active ingredients including, among many others, rotigotine may be used as the active principle of this formulation which may further contain wetting agents, binding agents, diluents, penetration enhancers and other ingredients. The penetration enhancers of this reference include, among many others, cyclodextrins. The administration routes described in this application are again multifold and comprise administration through the buccal mucosa, the nasal mucosa, the vaginal mucosa and sublingual administration. However, this reference does not specifically disclose an intranasal formulation of rotigotine and provides no teaching as to requirements and the necessary/suitable ingredients of such an intranasal formulation.

Apomorphine is a drug that shares certain functional features with rotigotine but is structurally different. Like rotigotine, apomorphine is a dopamine agonist and has therefore been used to treat various dopamine-related disorders, including morbus Parkinson. The nasal administration of apomorphine has also been tried. For example, WO 94/22445 describes pharmaceutical compositions for intranasal administration of apomorphine, morphine and dihydroergotamine. These drugs can be used in combination with saccharides or higher sugar alcohols.

J. Duarte et al. describe aspects of intranasal apomorphine in Parkinson's Disease in J. Pharmacol. Technol. 11:226-228 (1995). This report states on the one hand that intranasal administration of apomorphine is a comfortable and effective alternative to subcutaneous administration but on the other hand also mentions that one patient developed a nasal vestibulitis ("troublesome rhinitis") during chemical trials. While this patient could continue apomorphine therapy, doubts do remain of the general suitability of this therapy form when account is taken of the fact that only four patients participated in this study. A very similar report on such side effects is given in Ned Tijdschr Geneeskd 1992; 136, nr 14, p. 702. The authors of this reference suspect that apomorphine may bind as a hapten to proteins in the nasal mucosa and thus evoke an allergic reaction. Thus, even in the case of apomorphine, the problem of finding a safe (non-allergenic) and effective intranasal medication cannot be considered as having been solved satisfactorily.

More recently, the same findings with liquid intranasal formulations of apomorphine were confirmed again by Djupesland et al. in PFO Magazine, June/July 2002. These authors stated that while administration of liquid intranasal apomorphine has been shown to be effective in Parkinson's Disease, local side effects in the form of nasal crusting, inflammation and infection have been evident. In addition apomorphine was found to be subject to rapid oxidation in solution. To overcome these problems, a nasal-powder approach was developed.

OBJECTS OF THE INVENTION

The overriding objective of this invention is the development of a liquid intranasal formulation of rotigotine salts that is stable, safe and effective. Aspects of the desired stability include an acceptable oxidative stability and a good temperature stability. Aspects of formulation safety include, inter alia, no detectable microbiological contamination while retaining the possibility to avoid potentially irritating preservatives such as ethanol or benzalkonium chloride, even though such preservatives can be added according to necessity. However, in a preferred aspect of the present invention the intranasal formulation is free of any preservatives yet remains antibacterially active. Further aspects of safety include low irritation of the nasal mucosa and avoidance of nasal vestibulitis. Aspects of formulation efficacy include the possibility of administering sufficient quantities of rotigotine to a human subject suffering from Parkinson's Disease to achieve (a) a rotigotine plasma level in the order of at least 100 pg/ml and (b) a measurable improvement of the symptoms of Parkinson's Disease of at least 2 units in the Unified Parkinson's Disease Rating Scale (UPDRS) compared to a placebo treatment. In the context of this application, "placebo treatment" refers to a treatment with an intranasal composition of identical qualitative composition but where the active ingredient has been omitted.

SUMMARY OF THE INVENTION

Surprisingly it has been found that the above objectives could be obtained with a liquid intranasal pharmaceutical formulation comprising a pharmaceutically acceptable acid addition salt of rotigotine and α-cyclodextrin. The most preferred pharmaceutically acceptable acid addition salt of rotigotine is the hydrochloride. Further pharmaceutically acceptable acid addition salts that could be used include the urotrate, tartrate, citrate, phosphate, sulphate and the methanesulfonate. Additional preferred aspects of intranasal formulations according to the present invention are given in the appending dependent claims and in the following detailed description.

DETAILED DESCRIPTION OF THE INVENTION

According to preferred aspects of the present invention said liquid intranasal formulation further contains buffer salts, e.g. phosphates or acetates, and as such may be present as a buffered aqueous solution. In a preferred embodiment, the intranasal formulation contains phosphate buffered saline (PBS) as buffer system.

The intranasal formulation according to the present invention may preferably further contain a viscosity-enhancing substance. Glycerol and carboxymethylcellulose (CMC) are particularly useful as viscosity enhancers, but the present invention is not limited thereto. Glycerol is particularly preferred as it also has a soothing effect on the nasal mucosa. The viscosity of the intranasal formulations of the present invention should preferably be between 0.8 and 1.5 $mm^2/s$, most preferably around 1.2 $mm^2/s$. The viscosity can be determined by an Ubbelohde capillary viscosimeter with suspending ball-level for the determination of kinematic viscosity according to DIN 51562, part 1. Moreover, glycerol in the formulation surprisingly serves to increase the uptake of rotigotine through the nasal mucosa as was shown by in-vitro permeation assays with nasal mucosa from freshly slaughtered cattle.

The pH-value of the formulation of the present invention should preferably in the range of 4.5 to 6.5, more preferably around 5.8±0.3. The pH value of 5.8 leads to an optimal drug uptake as was revealed by in-vitro permeation assays. Surprisingly, a higher pH value of 6.5 as well as a lower pH value of 4.5 in the formulation resulted in a significantly lower rotigotine uptake through nasal mucosa tissue from freshly slaughtered cattle. The pH value of the intranasal formulation can be adjusted during or after its preparation with a pharmaceutically acceptable acid or base. Most preferably, citric acid is used for this purpose.

In a preferred aspect of the present invention the intranasal formulation does not contain a further absorption enhancer, preservative and/or antioxidant. While such agents are commonly used in many commercial intranasal preparations, the formulation of the present invention can do without them without sacrificing safety and efficacy, or even improve safety and efficacy by omitting such agents.

Nevertheless, according to a less preferred aspect of the invention, it is also possible that the intranasal formulation contains further absorption enhancers. Such enhancers can suitably be selected from surfactants and/or emulsifiers, particularly non-ionic surfactants such as polysorbate 80 (available for example under the trademark Tween™ 80) or PEG-40 hydrogenated castor oil (available for example under the trademark Cremophor™ RH40). As an antioxidant, the formulation may contain e.g. ascorbates or sorbates. Known preservatives that may, but do not need to be used in the formulation include antimicrobial substances such as benzalkonium chloride. It is one of the particularly advantageous and surprising features of the formulation according to the present invention that such antimicrobial preservatives are not needed, thus in a further aspect the present invention relates to an intranasal formulation as defined above that is free of preservatives. The absence of preservatives such as benzalkonium chloride provides an additional advantage because this agent shows a significant ciliary toxicity. Experiments conducted by the applicant show that even a formulation according to the invention that is free from preservatives shows no microbial contamination and satisfies the standards for topical formulations according to Ph. Eur., 4 Ed.

α-Cyclodextrin is a particularly important component of the present invention. The inventors have discovered that, unexpectedly, α-cyclodextrin markedly increases the storage stability of the intranasal formulation, even when compared to β-cyclodextrin. Moreover, α-cyclodextrin seems to have a much better solubility-enhancing effect on rotigotine hydrochloride than β-cyclodextrin. The concentration of α-cyclodextrin in solution does not need to be higher than 0.5 g/ml and is preferably in the range of 0.001-0.1 g/ml, more preferably between 0.05 and 0.1 g/ml and most preferably 0.05-0.085 g/ml.

Cyclodextrins per se, among many other agents, have been proposed for nasal drug delivery before, see e.g. Merkus et al in Advanced Drug Delivery Reviews 36 (1999) 41-57. However, the review of Merkus does not specifically address rotigotine and, on the whole, rather seems to prefer β-cyclodextrins and particularly methylated β-cyclodextrins. The article further notes large interspecies differences and cautions against blindly transferring the results of rat studies to humans.

The intranasal formulation according to a preferred aspect of the present invention may contain 1-6 mg/ml rotigotine-HCl in an aqueous buffered solution. According to a further and independent aspect of the present invention, the intranasal formulation contains between 0.03 and 0.1 g/ml α-cyclodextrin in the solution.

Particularly preferred intranasal formulations according to the present invention consist of 2-5 mg/ml rotigotine-HCl, 0.05-0.1 g/ml α-cyclodextrin and 2.2-3 vol. % glycerol in an aqueous buffer, such as phosphate buffered saline (PBS).

EXAMPLES

The following examples are to illustrate the invention without limiting it. All parts and percentages are volume-based unless indicated otherwise.

Example 1

The following intranasal formulation according to the present invention was prepared:

| | |
|---|---|
| 2.5 g/L | Rotigotine-HCl |
| 85 g/L | α-Cyclodextrin |
| 8 g/L | NaCl |
| 0.2 g/L | KCl |
| 1.44 g/L | $Na_2HPO_4 \times 2H_2O$ |
| 0.2 g/L | $KH_2PO_4$ |
| 31.2 g/L | Glycerol (87% solution in water) |
| water to add up to final volume | |

-continued citric acid for pH adjustment
pH of solution 5.8

610 ml water was adjusted to pH 3 with citric acid and alpha-cyclodextrin, glycerol and rotigotine hydrochloride were added to give a concentration of 85 mg/ml, 2.6 vol. % and 2.5 mg/ml respectively. Subsequently, 250 ml of 4×PBS buffer solution (having four times the concentration of standard PBS buffer solution, i.e. a concentration of 32 g/l NaCl, 0.8 g/l kCl, 5.76 g/l $Na_2HPO_4 \times 2H_2O$ and 0.8 g/l $KH_2PO_4$ in water) was added, followed by drop wise addition of 1 M citric acid until a pH of 5.8 was reached. Water was used to fill up to a final volume of 1000 ml.

The obtained solution was filtered through 0.22 μm PES filter. The solution may be filled in suitable pharmaceutical containers, e.g. dark vials of 8 ml volume, and is ready for intranasal administration to mammals, including man.

Example 2

The (maximum) solubility of rotigotine-HCl in aqueous solution at room temperature (20° C.) can be significantly improved by the use of α-cyclodextrin (α-CD) while there is no significant increase in rotigotine solubility when β-cyclodextrin is used. For cyclodextrin concentrations which are close to the maximum solubility of each of the two CD types, 5.03 mg/mL rotigotine-HCl could be dissolved in an 0.1 g/mL α-CD solution but only 1.57 mg/mL could be dissolved in a 0.015 g/mL β-CD solution.

The concentration was determined by isocratic HPLC analysis. HPLC column LiChroCART 75×4 mm, Superspher 60 RP-select B 5 μm (Merck), column temperature: 30° C., mobile phase: water/acetonitrile/methane sulfonic acid (65/35/0.05 v/v/v), flow rate: 2 mL/min, injection volume: 50 μl, detection at 220 nm, retention time approx. 1.5 min. The concentration was determined by use of an external reference solution with known concentration.

The results are shown in the following table 1:

TABLE 1

| CD-Concentration [g/mL] | Rotigotine hydrochloride [mg/mL] | | Rotigotine base [mg/mL] | |
|---|---|---|---|---|
| | α-CD | β-CD | α-CD | β-CD |
| 0 | 1.05 | 1.05 | 0.15 | 0.15 |
| 0.005 | n.d. | 1.34 | n.d. | 0.21 |
| 0.01 | 1.39 | 1.40 | 0.19 | 0.22 |
| 0.015 | n.d. | 1.57 | n.d. | 0.22 |
| 0.05 | 3.0 | * | 0.34 | * |
| 0.1 | 5.03 | * | 0.57 | * | n.d. = no data available
* = exceeds maximum β-CD solubility in the solution tested Very surprisingly, it was shown that the solubility of rotigotine hydrochloride is increased five-fold by adding 0.1 g/ml α-cyclodextrin (α-CD) whereas the maximum solubility-enhancing effect of β-CD was only very moderate (factor 1.6). Rotigotine base is practically insoluble both in aqueous solution and in aqueous solutions containing α- or β-cyclodextrin. The full beneficial effects of the present invention can therefore only be obtained by using α-cyclodextrin. This effect was surprising and unpredictable on the basis of the available data on rotigotine.

Example 3

To evaluate the storage stability of potential nasal formulations of rotigotine hydrochloride the following formulations were prepared:

Formulation Sample A

Comparative Example

| | |
|---|---|
| 2.5 g/L | Rotigotine-HCl |
| 0.5% (v/v) | Tween 80 |
| 8 g/L | NaCl |
| 0.2 g/L | KCl |
| 1.44 g/L | $Na_2HPO_4 \times 2H_2O$ |
| 0.2 g/L | $KH_2PO_4$ |
| water to add up to final volume | |
| citric acid for pH adjustment, pH 5.8 | |

470 ml water were adjusted to pH 3 with citric acid and Tween 80 and rotigotine hydrochloride were added to give a concentration of 0.5 vol. % and 2.5 mg/ml respectively. Subsequently, 200 ml of 4×PBS buffer solution was added, followed by drop wise addition of 1 M citric acid until a pH of 5.8 was reached. Water was used to fill up to a final volume of 800 ml.

Formulation Sample B

Inventive Formulation

| | |
|---|---|
| 2.5 g/L | Rotigotine-HCl |
| 85 g/L | α-Cyclodextrin |
| 8 g/L | NaCl |
| 0.2 g/L | KCl |
| 1.44 g/L | $Na_2HPO_4 \times 2H_2O$ |
| 0.2 g/L | $KH_2PO_4$ |
| water to add up to final volume | |
| citric acid for pH adjustment, pH 5.8 | |

470 ml water was adjusted to pH 3 with citric acid and α-cyclodextrin and rotigotine hydrochloride were added to give a concentration of 85 mg/ml and 2.5 mg/ml respectively. Subsequently, 200 ml of 4×PBS buffer solution were added, followed by drop wise addition of 1 M citric acid until a pH of 5.8 was reached. Water was used to fill up to a final volume of 800 ml.

The stability was determined by measuring the concentration of rotigotine over time using gradient HPLC analysis.

HPLC column: Licrospher 100 CN, 5 μm, 125×4.6 mm (Bidhoff), pre column filter: 2 μm, mobile phase A: water/methane sulfonic acid (1000/0.5 (v/v)), mobile phase B: acetonitrile/methane sulfonic acid 1000/0.5 (v/v)), flow rate 1.0 mL/min, profile of the gradient: 0 min 95% A/5% B; 2 min 95% A/5% B; 35 min 40% A/60% B; 38 min 40% A/60% B; 39 min 95% A/5% B; initial pressure approx. 90 bar, injection volume 80 μl, detection at 220 nm and 272 nm, retention time approx. 18 min. All peaks in the chromatogram with an area >0.05% were integrated up to a retention time of 35 minutes to calculate the purity of the drug substance. The relative purity is used to calculate the degradation of Rotigotine hydrochloride. The results are shown in Table 2.

TABLE 2

|  | Sample A (Tween 80, without α-CD) | | Sample B (with α-CD) | |
| --- | --- | --- | --- | --- |
|  | 220 nm | 272 nm | 220 nm | 272 nm |
| Rotigotine degradation * 6 weeks 60° C. | −5, 6 | −11, 1 | −1, 0 | −5, 6 |
| Rotigotine degradation * 1 year 40° C. | −6, 0 | −9, 1 | −0, 4 | −2, 0 |
| Rotigotine degradation * 1 year 25° C. | −2, 6 | −3, 1 | ±0.0 | +0.2** |

* These values reflect the loss in rotigotine absorption between the start values and the actual test points at the given conditions.
**The apparent increase in purity can be explained by the measurement accuracy of the analytical method. The result should be interpreted as no significant change in purity relative to the starting value at t = 0.

It is readily apparent from Table 2 that α-cyclodextrin (sample B) markedly increased stability of rotigotine hydrochloride as compared to the Tween 80 formulation (sample A). The stabilizing effect of α-cyclodextrin becomes also apparent from a comparative test in an aqueous rotigotine solution. Following storage at 60° C. for 8 weeks, a rotigotine solution of 1.6 mg/ml with α-cyclodextrin showed a decrease in the rotigotine concentration of −0.07 mg/ml, whilst a solution of 1.9 mg/ml of rotigotine without α-cyclodextrin showed a decrease of −0.22 mg/ml.

Example 4

| | |
| --- | --- |
| 2.5 g/L | Rotigotine-HCl |
| 50 g/L | α-Cyclodextrin |
| 4 g/L | NaCl |
| 0.1 g/L | KCl |
| 0.72 g/L | $Na_2HPO_4 \times 2H_2O$ |
| 0.1 g/L | $KH_2PO_4$ |
| 31.2 g/L | Glycerol (87% solution in water) |

470 ml water was adjusted to pH 3 with citric acid and α-cyclodextrin, glycerol and rotigotine hydrochloride were added to give a concentration of 50 mg/ml and 2.5 mg/ml, respectively.

Subsequently, 200 ml of 2×PBS buffer solution were added, followed by drop wise addition of 1 M citric acid until a pH of 5.8 was reached. Water was used to fill up to a final volume of 800 ml.

The invention claimed is:

1. A liquid intranasal pharmaceutical formulation comprising a pharmaceutically acceptable acid addition salt of rotigotine and α-cyclodextrin.
2. The formulation of claim 1, further comprising a buffer system.
3. The formulation of claim 2, wherein the buffer system is phosphate buffered saline.
4. The formulation of claim 1, further comprising a viscosity-enhancing substance effective to give a viscosity of 0.5-1.5 $mm^2/s$.
5. The formulation of claim 4, wherein the viscosity-enhancing substance is glycerol.
6. The formulation of claim 1, having a pH of 5-6.5.
7. The formulation of claim 1, further comprising a pharmaceutically acceptable acid for adjustment of pH.
8. The formulation of claim 7, wherein the pharmaceutically acceptable acid is citric acid.
9. The formulation of claim 1 that does not contain any preservative.
10. The formulation of claim 1 that does not contain any antioxidant.
11. The formulation of claim 1, further comprising an absorption enhancer selected from non-ionic surfactants.
12. The formulation of claim 11, wherein the absorption enhancer is polysorbate 80 or PEG-40 hydrogenated castor oil.
13. The formulation of claim 1, wherein the pharmaceutically acceptable acid addition salt of rotigotine is rotigotine hydrochloride.
14. The formulation of claim 13, comprising 1-6 mg/ml rotigotine hydrochloride in an aqueous buffered solution.
15. The formulation of claim 13, comprising between 0.03 and 0.1 g/ml α-cyclodextrin in an aqueous buffered solution.
16. The formulation of claim 3, wherein the formulation comprises 2-5 mg/ml rotigotine hydrochloride, 0.05-0.1 g/ml α-cyclodextrin and 2.2-3% glycerol in phosphate buffered saline.
17. The formulation of claim 16, further comprising citric acid in an amount effective to adjust pH of the formulation to a value of 5-6.5.

* * * * *